(12) United States Patent
Mühlbauer et al.

(10) Patent No.: US 8,785,447 B2
(45) Date of Patent: *Jul. 22, 2014

(54) USE OF DOPAMINE $D_3$ RECEPTOR LIGANDS FOR THE PRODUCTION OF DRUGS FOR TREATING RENAL FUNCTION DISORDERS

(75) Inventors: Bernd Mühlbauer, Rottenburg (DE); Gerhard Groβ, Speyer (DE); Dorothea Starck, Ludwigshafen (DE); Hans-Jörg Treiber, Brühl (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 1241 days.

This patent is subject to a terminal disclaimer.

(21) Appl. No.: 11/424,739

(22) Filed: Jun. 16, 2006

(65) Prior Publication Data

US 2006/0223793 A1    Oct. 5, 2006

Related U.S. Application Data

(62) Division of application No. 09/959,787, filed as application No. PCT/EP00/03865 on Apr. 28, 2000, now Pat. No. 7,098,214.

(51) Int. Cl.
*A61K 31/497* (2006.01)
(52) U.S. Cl.
USPC ................. 514/252.14; 514/252.19
(58) Field of Classification Search
None
See application file for complete search history.

(56) References Cited

U.S. PATENT DOCUMENTS

| | | | | |
|---|---|---|---|---|
| 3,270,004 | A | 8/1966 | Alter | 260/239 |
| 6,214,822 | B1 | 4/2001 | Treiber et al. | 514/218 |
| 6,342,604 | B1 * | 1/2002 | Hellendahl et al. | 544/300 |
| 7,098,214 | B1 * | 8/2006 | Muhlbauer et al. | 514/252.19 |

FOREIGN PATENT DOCUMENTS

| | | |
|---|---|---|
| DE | 42 23 921 | 1/1994 |
| WO | WO 97/25324 | 7/1997 |

OTHER PUBLICATIONS

Berge et al. Pharmaceutical Salts. Journal of Pharmaceutical Sciences. vol. 66, No. 1, Jan. 1988, pp. 1-19.*
Lulppold et al., Naunyn-Schmiedeberg's Arch Pharmacol 358 690-693 (1998): "*Dopamine $D_3$ receptio activation modulated renal function in anesthetized rats*".
Barilli et al., Clinical and Experimental Pharmacology and Physiology, 26, S67 (1999): "Micro-anatomical Localization of the Dopamine $D_3$ Receptor Subtype in the Rat Kidney".
Hussain et al., Hypertension 32,187-197 (1998): "*Renal Dopamine Receptor Function in Hy-pertension*".
Murray et al., Bioorganic & Medical Chemistry Letters 5, 219-222 (1995): "*A Novel Series of Arylpiperazines with High Affinity ans Selectivity for the Dopamine $D_3$ Receptor*".
Asico et al., J. Clin. Invest 102, 493-498 (1998): "*Disruption of the Dopamine $D_3$ Receptor Gene Produces Renin-dependent Hypertension*".
Luippod et al., Kidney Blood Press, Res. 21, 113 (1998): "*Renal Effects of Dopamine $D_3$ Rec-ceeptor Activation un Spontaneously Hypertensive Rats*".
O'Connell et al., Hypertension32, 886-895 (1998): "*Expression of the Dopamine $D_3$ Receptor Protein in the Rat Kidney*".
Luippold et al., Naunyn-Schmiedeberg's Arch Pharmacol 357 (4 Suppl), R116 (1998): "*Increase of renal vascular resistance by dopamine $D_3$-receptor activation in anesthetized rats*" (abstract).
Lear et al., Renal Disorders in Sickle Hemoglobinemia, in Therapy of Renal Diseases and Related Disorders, W.N. Suki and S.G. Massry, eds., at pp. 573-575 (1991).

* cited by examiner

*Primary Examiner* — Anna Pagonakis
(74) *Attorney, Agent, or Firm* — Lisa V. Mueller; Michael Best & Friedrich LLP

(57) ABSTRACT

The invention relates to the use of dopamine $D_3$ receptor ligands for the production of drugs for treating renal function disorders.

25 Claims, No Drawings

USE OF DOPAMINE D₃ RECEPTOR LIGANDS FOR THE PRODUCTION OF DRUGS FOR TREATING RENAL FUNCTION DISORDERS

CROSS-REFERENCE TO RELATED APPLICATIONS

This is a divisional of U.S. patent application Ser. No. 09/959,787, filed on Nov. 7, 2001, now U.S. Pat. No. 7,098,214, which is a U.S. national stage entry of International Patent Application No. PCT/EP2000/003865, filed on Apr. 28, 2000, which claims priority to German Patent Application No. 19922443.9, filed on May 7, 1999, the entire contents of all of which are fully incorporated herein by reference.

BACKGROUND OF THE INVENTION

The present invention relates to the use of selective dopamine $D_3$ receptor ligands for the production of drugs for treating renal function disorders.

The present invention relates to the use of selective dopamine $D_3$ receptor ligands for the production of drugs for treating renal function disorders.

Preferred receptor ligands are receptor antagonists.

In particular, the invention relates to drugs for the treatment of renal function disorders in which a disorder of the glomerular filtration rate in the sense of glomerular hyperfiltration occurs.

It is regarded as proven that the dopamine $D_3$ receptor is expressed in the kidney, in particular in the nephron (cf. D. P. O'Connell et al., Hypertension, 1998, 32, 886).

It is regarded as proven that the dopamine $D_3$ receptor is expressed in the kidney, in particular in the nephron (cf. D. P. O'Connell et al., Hypertension, 1998, 32, 886).

DE-A 4223921 very generally describes the use of dopamine receptor antagonists, without indication of specific subtypes, in the therapy of the progressive worsening of kidney function.

In Naunyn-Schmiedeberg's Arch. Pharmacol (1998) 358: 690-693, G. Luippold et al. describe investigations with respect to the influence of specific $D_2$ and $D_3$ receptor antagonists on the renal hemodynamics and excretion function in a purely artificial functional state without pathophysiological changes.

L. D. Asico et al., J. Clin. Invest., Vol. 102 (1998), 493-498, describe that blockade of the $D_3$ receptor results in increased renin production, renal sodium retention and, as a result, renin-dependent hypertension.

Sclerosing processes in the glomerular capillaries and disorders of the filtration rate caused thereby occur in disorders such as diabetes mellitus, hypertension, infectious or noninfectious glomerulonephritis, ascending urinary tract infections, sickle cell anemia, or compensatory hypertrophy after unilateral kidney resection.

The progressive worsening of the kidney function relates to nearly all patients with glomerulonephritis and more than one third of all patients with diabetes mellitus.

Kidney functional disorders occur as a result of glomerulosclerosis, which is also described as diabetic nephropathy, which is characterized histologically by a diffuse thickening of the glomerular capillaries and an alteration of the mesangium as a result of diffuse intercalation of basal membrane-like material or spherical fibrinous intercalations. As a result, an alteration of the filtration action occurs in the sense of hyperfiltration.

In glomerulonephritis too, a change in the glomerular basal membranes occurs and, as a result, a disorder of the filtration rate.

SUMMARY OF THE INVENTION

It was the object of the present invention to find drugs which make possible targeted therapy of the renal function disorders in the case of the diseases mentioned.

Accordingly, the use of selective dopamine $D_3$ receptor ligands for the production of drugs for treating renal function disorders has been found. Renal function disorders include
renal function disorders with glomerular hyperfiltration,
renal function disorders caused by diabetes mellitus,
renal function disorders caused by nonrenal hypertension,
renal function disorders caused by glomerulonephritis,
renal function disorders caused by ascending urinary tracts infections,
renal function disorders caused by compensatory hypertrophy after unilateral nephrectomy, and
renal function disorders caused by mesangial dysfunction.

DETAILED DESCRIPTION OF THE INVENTION

Suitable dopamine $D_3$ receptor ligands are basically all compounds having an affinity for this receptor, preferably those compounds which have an affinity for this receptor which is larger by a factor of 10 in comparison with another dopamine receptor.

Suitable compounds are, for example, the selective dopamine $D_3$ receptor ligands mentioned in the following documents: 2-aminoindans as described in WO 95/04713, benzimidazoles as disclosed in WO 95/30658, 2-aminotetralins as disclosed in EP-A 286516 and Bioorg. Med. Chem. Lett. 1997, 7, 881, as well as the compounds disclosed in WO 94/21608, WO 96/30333, Bioorg. Med. Chem. Lett. 1996, 6, 6403, or J. Med. Chem., 1996, 39, 4233.

Tetrahydroisoquinoline derivatives, such as are described in the documents WO 97/43262, WO 98/51671, WO 98/50363, WO 98/49145, WO 98/50364 or WO 98/06699 are furthermore suitable, and also the compounds disclosed in WO 97/17326 or WO 97/47602.

The compounds mentioned in the documents WO 97/34884, Bioorg. Med. Chem. Lett. 1997, 7, 2403, EP-A 779584, WO 98/18798, or WO 96/02520, WO 96/02519, WO 96/02249, WO 96/02246, WO 97/00106 and WO 98/04138 are likewise suitable.

Compounds of the general formula I $$L\text{-}D\text{-}E \qquad (I)$$

in which
L is
  a 5- or 6-membered aromatic hetero monocyclic system L1 having 1, 2 or 3 heteroatoms, which independently of one another are selected from O, N and S,
or an aromatic or heteroaromatic ring selected from the group L2

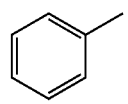 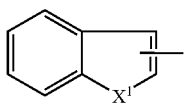

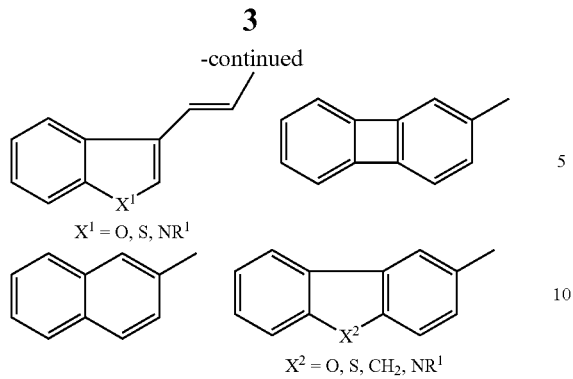

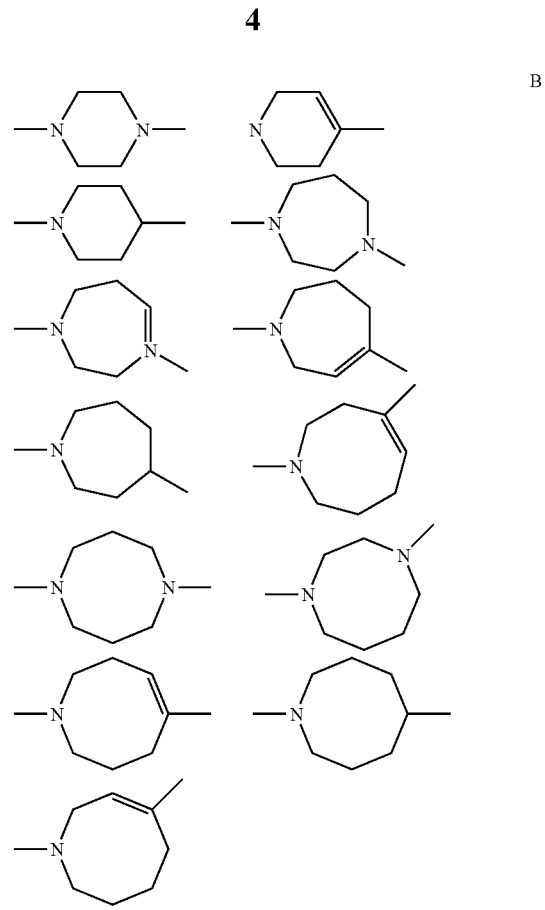

where L optionally has 1, 2, 3 or 4 substituents, which independently of one another are selected from $OR_1$, $C_1$-$C_6$-alkyl which is optionally substituted by OH, $OC_1$-$C_6$-alkyl, phenyl or halogen, such as $CF_3$, $CHF_2$, $C_2$-$C_6$-alkenyl, $C_2$-$C_6$-alkynyl, $C_3$-$C_8$-cycloalkyl, halogen, CN, $CONR^1R^2$, $CO_2R^1$, $NO_2$, $NR^1R^2$, $SR^1$, $SO_2R^1$, $SO_2NR^1R^2$, $OSO_2R^1$, Ax1 or phenoxy which is optionally substituted by $C_1$-$C_6$-alkyl, $OC_1$-$C_6$-alkyl or halogen, or $C_1$-$C_6$-alkanoyl or benzoyl;

in which

Ax1 is phenyl, naphthyl or a 5- or 6-membered heterocyclic aromatic ring having 1 to 4 heteroatoms which are selected from O, S and N, where Ax1 optionally has 1, 2, 3 or 4 substituents which independently of one another are selected from $C_1$-$C_6$-alkyl which is optionally substituted by OH, $OC_1$-$C_6$-alkyl, halogen or phenyl, $C_1$-$C_6$-alkoxy, $C_2$-$C_6$-alkenyl, $C_2$-$C_6$-alkynyl, $C_3$-$C_6$-cycloalkyl, halogen, CN, $COOR^1$, $NR^1R^2$, $NO_2$, $SR^1$, $SO_2R^2$, $SO_2NR^1R^2$, or phenyl which is optionally substituted by $C_1$-$C_6$-alkyl, $OC_1$-$C_6$-alkyl, $NR^2R^2$, CN, $CF_3$, $CHF_2$, or halogen, and where the heterocyclic, aromatic ring mentioned can optionally be fused to a phenyl ring;

$R^1$ is H, $C_3$-$C_6$-cycloalkyl, or $C_1$-$C_6$-alkyl, which is optionally substituted by OH, $OC_1$-$C_6$-alkyl, phenyl or halogen, for example as $CF_3$ or $CHF_2$; the radicals $R^2$, which can be identical or different, have the meanings indicated for $R^1$ or are $COR^1$ or $CO_2R^1$;

$R^3$ is Ax1, $OR^1$, $R^1$, $C_2$-$C_6$-alkenyl, $C_2$-$C_6$-alkynyl, Hal, CN, $CONR^1R^1$, $COOR^1$, $NO_2$, $NR^1R^1$, $SR^1$, $OSO_2R^1$, $SO_2R^1$, $R^4$ to $R^6$ independently of one another are H, $C_1$-$C_6$-alkyl, $OR^1$, CN, $NR^2R^2$, $SR^1$, $CF_3$;

$R^7$ is H, $C_1$-$C_6$-alkyl, $C_3$-$C_6$-cycloalkyl or phenyl;

D is a $CONR^7$—$C_3$-$C_{10}$-alkylene group if L is L2, or, if L is a 5- or 6-membered aromatic heteromonocyclic system L1, D is a $C_4$-$C_{10}$-alkylene group or a $C_3$-$C_{10}$-alkylene group, which comprises at least one group Z which is selected from —$CH_2$—, O, S, $NR^1$, $C_3$-$C_6$-cycloalkyl, CO, $CONR^1$, a double bond and a triple bond, where $R^1$ is as defined above, E is one of the radicals of the formula (E1) or (E2) and (E1) is B-G, in which B is a 6-, 7- or 8-membered saturated ring having one or two nitrogen heteroatoms, where the nitrogen heteroatoms are situated in the 1,4- or 1,5-position and the ring is bonded to the radical D in the 1-position and to the radical G in the 4- or 5-position and where the ring can moreover have a double bond in the 3- or 4-position;

in which

G is phenyl, pyridyl, pyrimidinyl or triazinyl, where G can optionally have 1 to 4 substituents which independently of one another are selected from $OR^1$, alkyl, $C_2$-$C_6$-alkenyl, $C_2$-$C_6$-alkynyl, alkoxyalkyl, haloalkyl, halogen, CN, $CO_2R^1$, $NO_2$, $SO_2R^1$, $NR^1R^2$, $SO_2NR^1R^2$, $SR^1$, a 5- or 6-membered carbocyclic, aromatic or nonaromatic ring and a 5- or 6-membered heterocyclic aromatic or nonaromatic ring having 1 or 2 heteroatoms, which are selected from O, S and N, where the carbocyclic or the heterocyclic ring is optionally substituted by $C_1$-$C_6$-alkyl, phenyl, phenoxy, halogen, $OC_1$-$C_6$-alkyl, OH, $NO_2$ or $CF_3$, where G can optionally be fused to a carbocyclic or heterocyclic ring of the type defined above;

and (E2) is one of the radicals E2a to E2d

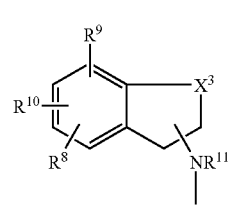

E2a

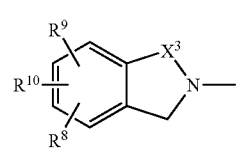

E2b

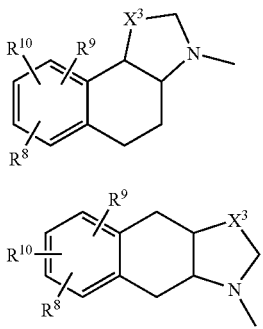

in which $X^3$ is $CH_2$ or $CH_2CH_2$;

$R^{11}$ is H, $C_1$-$C_6$-alkyl which is optionally substituted by OH, $OC_1$-$C_6$-alkyl, phenyl or halogen, $C_3$-$C_6$-cycloalkyl, optionally halogen-substituted (1 or 2 halogen atoms) $C_2$-$C_6$-alkenyl, or $C_2$-$C_6$-alkynyl;

$R^8$, $R^9$ and $R^{10}$ independently of one another are selected from H, $C_1$-$C_6$-alkyl which is optionally substituted by OH, $OC_1$-$C_6$-alkyl, $C_1$-$C_6$-alkylthio, halogen or phenyl, OH, $C_1$-$C_6$-alkoxy, SH, $C_1$-$C_6$-alkylthio, $C_2$-$C_6$-alkenyl, $C_2$-$C_6$-alkynyl, halogen, CN, $NO_2$, $SO_2R^1$, $OSO_2R^1$, $SO_2NR^1R^1$, $NHSO_2R^1$, $NR^1R^2$, a 5- or 6-membered carbocyclic, aromatic or nonaromatic ring and a 5- or 6-membered heterocyclic aromatic or nonaromatic ring having 1 or 2 heteroatoms, which independently of one another are selected from O, S and N, where the carbocyclic or the heterocyclic ring can have 1 or 2 substituents which independently of one another are selected from $C_1$-$C_6$-alkyl, phenyl, phenoxy, halogen, $C_1$-$C_6$-alkoxy, OH, $NO_2$, $CF_3$ and $CHF_2$ and where two of the substituents $R^8$, $R^9$ and $R^{10}$ together with the carbon atoms of the phenyl ring to which they are bonded can form a phenyl, cyclopentyl or cyclohexyl ring fused onto the phenyl ring; and their salts with physiologically tolerable acids.

In the context of the present invention, the following expressions have the meanings indicated below:

Alkyl (also in radicals such as alkoxy, alkylamino etc.) is a straight-chain or branched alkyl group having 1 to 6 carbon atoms and in particular 1 to 4 carbon atoms. The alkyl group can have one or more substituents which independently of one another are selected from OH, $OC_1$-$C_6$-alkyl, halogen or phenyl.

Examples of an alkyl group are methyl, ethyl, n-propyl, i-propyl, n-butyl, isobutyl, t-butyl, etc.

Cycloalkyl is in particular $C_3$-$C_6$-cycloalkyl, such as cyclopropyl, cyclobutyl, cyclopentyl and cyclohexyl.

Alkylene is straight-chain or branched radicals. If D has no group Z, D comprises from 4 to 10 carbon atoms, preferably from 4 to 8 carbon atoms. The chain between L and group E then has at least four carbon atoms. If one of the groups mentioned contains Z, D comprises from 3 to 10 carbon atoms, preferably from 3 to 8 carbon atoms.

The alkylene groups can optionally comprise one of the groups Z indicated above in the definition of D. This can be arranged—just like the double or triple bond mentioned—in the alkylene chain in any desired place or in position 1 or 2 of the group D (seen from the radical L). The radicals $CONR^1$ and COO are preferably arranged such that the carbonyl group faces the group L1 in each case.

Particularly preferably, D represents compounds as in the formula I, in which D is —Z—$C_3$-$C_6$-alkylene, in particular —Z—$CH_2CH_2CH_2$—, —$ZCH_2CH_2CH_2CH_2$—, —Z—$CH_2CH$=$CHCH_2$—, —Z—$CH_2C(CH_3)$=$CHCH_2$—, —Z—$CH_2C$(=$CH_2$)$CH_2$—, —Z—$CH_2CH$ ($CH_3$)$CH_2$— or a linear —Z—$C_7$-$C_{10}$-alkylene radical. Z can in this case also be $CH_2$ and is preferably $CH_2$, O and in particular S.

Halogen is generally F, Cl, Br or I, preferably F or Cl.

Haloalkyl can comprise one or more, in particular 1, 2, 3 or 4, halogen atoms, which can be situated on one or more C atoms, preferably in the α- or ω-position. $CF_3$, $CHF_2$, $CF_2Cl$ or $CH_2F$ are particularly preferred.

Acyl is preferably HCO or $C_1$-$C_6$-alkyl-CO, in particular acetyl.

If L is substituted, the substituent can also be situated on the nitrogen heteroatom.

Preferably, L is a group of the formula

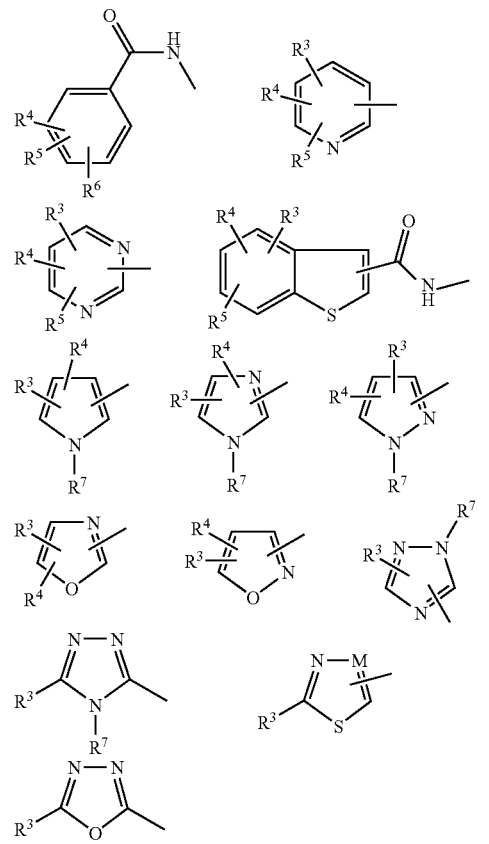

in which $R_3$ is Ax1, $OR^1$, $R^1$, $C_2$-$C_6$-alkenyl, $C_2$-$C_6$-alkynyl, Hal, CN, $CONR^1R^1$, $COOR^1$, $NR^1R^2$, $SR^1$, $SO_2R^1$, $R^4$ to $R^6$ independently of one another are H, $C_1$-$C_6$-alkyl, $OR^1$, CN, $NR^2R^2$, $SR^1$, $CF_3$, $R^7$ is H, $C_1$-$C_6$-alkyl or $C_3$-$C_6$-cycloalkyl and M is N or CH.

Ax1 is preferably a substituent of the formula

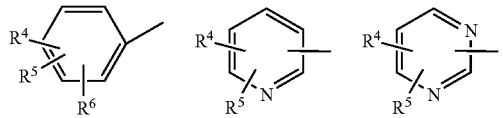

-continued

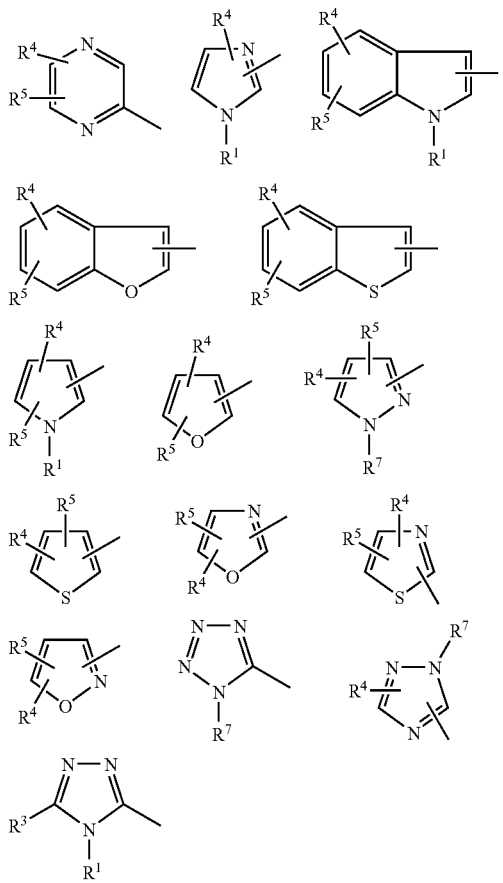

in which
$R^4$ to $R^6$ have the meanings indicated above and
$R^7$ is preferably $C_1$-$C_4$-alkyl.
Particularly preferably, L is

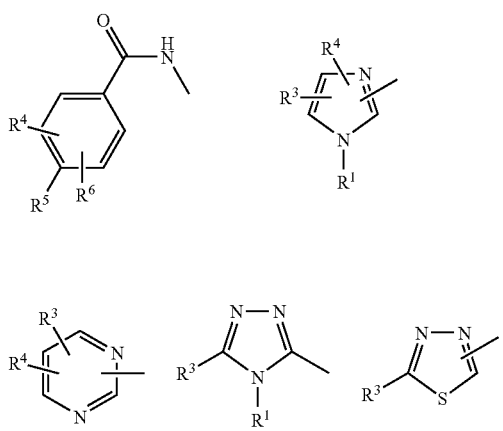

in which
$R^3$ is Ax1, $R^1$, COOR$^1$, NO$_2$, NR$^1$R$^2$, SR$^1$, OSO$_2$CF$_3$, SO$_2$R$^1$, CF$_3$, CHF$_2$,
$R^4$ to $R^6$ is H, $C_1$-$C_6$-alkyl, OR$^1$, NR$^2$R$^2$, and
$R^7$ is H, $C_1$-$C_6$-alkyl.

Ax1 is particularly preferably

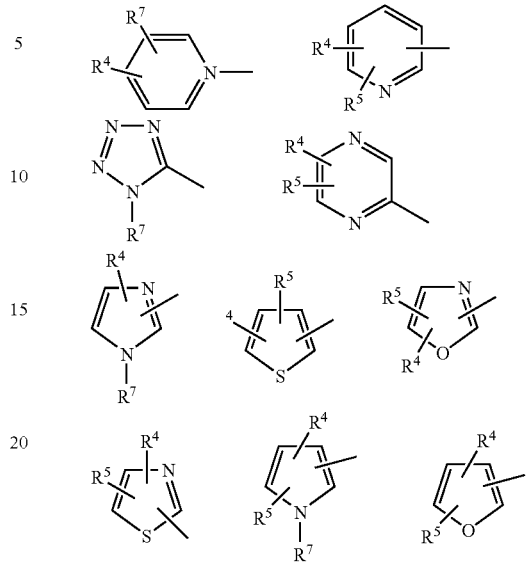

The phenyl, pyrazinyl, thiazolyl and pyrrolyl radicals indicated are particularly preferred in which $R^4$, $R^5$ and $R^7$ have the meanings indicated above.

According to one embodiment, the invention relates to the use of compounds of the formula (I) in which E represents the abovementioned radicals (E2) and L and D have the meaning indicated above.

L is then preferably an L1a

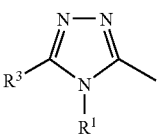

(L1a)

Particularly preferably, E is E2b in which X$^3$ is preferably CH$_2$CH$_2$ or E2c, in which X$^3$ is preferably CH$_2$, and L is then particularly preferably a 1,2,4-(4H)-triazole which carries a substituent Ax1 in the 3-position and a radical $R^7$ in the 4-position.

If E is a group E2b, E2c or E2d, D is preferably $C_4$-$C_{10}$-alkylene or $C_3$-$C_{10}$-alkylene which comprises at least one group Z which is selected from O, S, CO, —CH$_2$—, a double bond and a triple bond.

Preferably, at least one of the radicals $R^8$, $R^9$ and $R^{10}$ is H.

The radicals $R^8$, $R^9$ and $R^{10}$ are preferably and independently of one another selected from H, $C_1$-$C_6$-alkyl, OH, $C_1$-$C_6$-alkoxy, OSO$_2$R$^1$, $C_1$-$C_6$-alkylthio-$C_1$-$C_6$-alkyl and halogen. Particularly preferably, the phenyl group has one or two substituents, i.e. one or two of the radicals $R^8$, $R^9$ and $R^{10}$ are $C_1$-$C_6$-alkyl, OH, $C_1$-$C_6$-alkoxy or halogen.

If one of the radicals $R^8$, $R^9$ and $R^{10}$ is a 5- or 6-membered heterocyclic ring, it is, for example, a pyrrolidine, piperidine, morpholine, pyridine, pyrimidine, triazine, pyrrole, thiophene or pyrazole radical, a pyrrole, pyrrolidine, pyrazole or thienyl radical being preferred.

If one of the radicals $R^8$, $R^9$ and $R^{10}$ is a carbocyclic radical, it is in particular a phenyl, cyclopentyl or cyclohexyl radical.

The group E is preferably a group of the formula (E1) where (E1) is B-G

B is then preferably a radical of the formula (B1)

(B1)

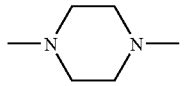 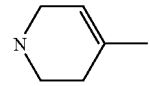

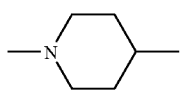 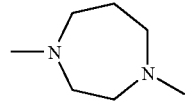

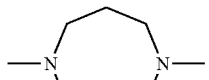 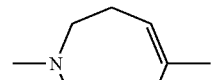

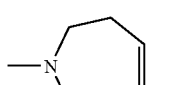 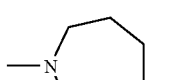

and particularly preferably (B2)

(B2)

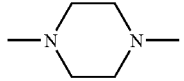 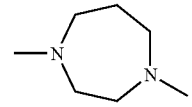

The radical G can have one, two, three or four substituents, preferably one or two substituents, which are situated, in particular, in the m-position and/or p-position. Preferably, they are independently of one another selected from $C_1$-$C_6$-alkyl, haloalkyl, $NO_2$, halogen, in particular chlorine, phenyl, pyrrolyl, imidazolyl, pyrazolyl, thienyl, cyclopentyl and cyclohexyl. If one of the substituents is $C_1$-$C_6$-alkyl, a branched group and in particular isopropyl or t-butyl is preferred.

Preferably, G is optionally substituted phenyl, 2-, 3- or 4-pyridinyl or 2-, 4(6)- or 5-pyrimidinyl.

If one of the substituents of the radical G is a 5- or 6-membered heterocyclic ring, it is, for example, a pyrrolidine, piperidine, morpholine, pyridine, pyrimidine, triazine, pyrrole, thiophene, thiazole, imidazole, oxazole, isoxazole, pyrazole or thiadiazole radical, a pyrrole, imidazole, pyrazole or thienyl radical being preferred.

If one of the substituents of the radical G is a carbocyclic radical, it is in particular a phenyl, cyclopentyl or cyclohexyl radical.

If G is fused to a carbocyclic radical, it is in particular a naphthalene, di- or tetrahydronaphthalene radical.

Particularly preferred compounds of the formula I are those in which L is selected from

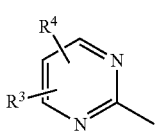 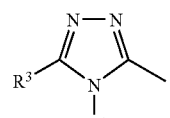

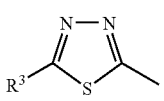 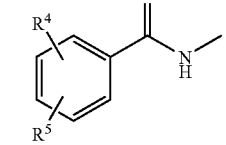

and D is —Z—(CH$_2$)$_3$— or —Z—(CH$_2$)$_4$—, and E is B1-G, R$^3$, R$^4$, R$^7$, Z, B1 and G having the meanings indicated above.

Very particularly preferred compounds for the purposes of this invention are those in which
  L is selected from

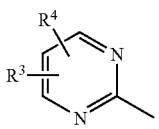 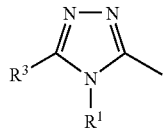

D is —Z—(CH$_2$)$_3$— or —Z—(CH$_2$)$_4$—,
B is

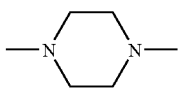 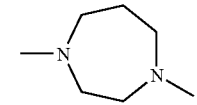

in particular

and
  G is 4-pyrimidyl, and the other radicals have the above-mentioned meaning, and in the case where L is triazolyl, R$^3$ is preferably

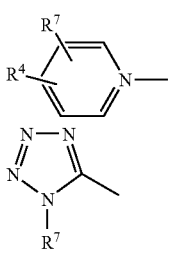 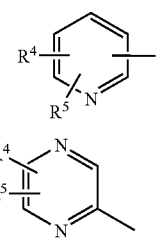

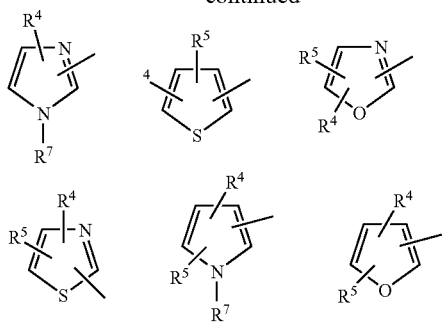

or NR$^1$R$^1$, where R$^1$ can be identical or different.

The invention also comprises the acid addition salts of the compounds of the formula I with physiologically tolerable acids. Suitable physiologically tolerable organic and inorganic acids are, for example, hydrochloric acid, hydrobromic acid, phosphoric acid, sulfuric acid, oxalic acid, maleic acid, fumaric acid, lactic acid, tartaric acid, adipic acid or benzoic acid. Further utilizable acids are described in Fortschritte der Arzneimittelforschung, [Advances in Pharmaceutical Research], Volume 10, Pages 224 ff, Birkhäuser Verlag, Basle and Stuttgart, 1966.

The compounds of the formula I can have one or more asymmetric centers. The invention therefore includes not only the racemates, but also the relevant enantiomers and diastereomers. The respective tautomeric forms are also included in the invention.

The process for the preparation of the compounds of the general formula (I) consists in a) reacting a compound of the general formula (II)

L-D-Y$^1$  (II)

in which Y$^1$ is a customary leaving group such as, for example, Hal, alkanesulfonyloxy, arylsulfonyloxy etc., and Z has the abovementioned meanings, with a compound of the general formula (III)

H-E  (III);

or b) reacting a compound of the general formula (IV)

L-D1-Z$^1$H  (IV)

in which Z$^1$ is O, NR$^1$ or S and D1 is C$_1$-C$_{10}$-alkylene or a bond, with a compound of the general formula V

Y$^1$-D2-E  (V)

where Y$^1$ has the meaning indicated above and D2 is C$_2$-C$_{10}$-alkylene, D1 and D2 together having 3 to 10 C atoms;

or c) reacting a compound of the general formula (VI)

L-Y$^1$  (VI)

in which Y$^1$ has the meaning indicated above, with a compound of the general formula VII

H—Z$^1$-D-E  (VII)

in which Z$^1$ has the meanings indicated above; or d) converting a compound of the formula (VIII)

NC-D-E  (VIII)

into a compound of the type (IX)

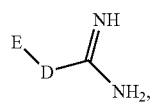

(IX)

and reacting this with a dicarbonyl compound in a known manner, e) "Umpolung" (reversing the polarity) of a compound of the general formula (X)

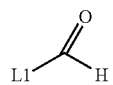

(X)

using reagents known from the literature, such as, for example, 1,3-propanedithiol, KCN/water, TMSCN (trimethylsilyl cyanide) or KCN/morpholine, as, for example, described in Albright, *Tetrahedron,* 1983, 39, 3207 or D. Seebach, *Synthesis* 1969, 17 and 1979, 19 or H. Stetter, *Angew. Chem. Int.* Ed. 1976, 15, 639 or van Niel et al., *Tetrahedron* 1989, 45, 7643

Martin et al., *Synthesis* 1979, 633, to give the products (Xa) (for example with 1,3-propanedithiol)

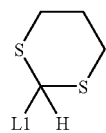

(Xa)

and then chain-lengthening them using compounds of the general formula (XI)

Y$^1$-D3-E  (XI)

where Y$^1$ has the meanings indicated above and D3 is C$_3$-C$_9$-alkylene which can contain a group Z, where, after deprotection or reduction, compounds of the formula (Ia)

T-Z$^3$-D2-E  (Ia)

in which Z$^3$ is CO or a methylene group and Z$^3$ and D2 together have 4 to 10 C atoms, are obtained; or g) reacting a compound of the formula (X) with a compound of the general formula (XII)

Y$^3$-D-E  (XII)

in which Y$^3$ is a phosphorane or a phosphonic ester, analogously to customary methods, as described, for example, in Houben-Weyl "*Methoden der Organischen Chemie*" [Methods of Organic Chemistry], 4$^{th}$ Edition, Thieme Verlag Stuttgart, Volume V/1b p. 383 ff or Vol, V/1c p. 575 ff.

The process for the preparation of a compound of the formula I which comprises the group COO or CONR$^7$ consists in reacting a compound of the general formula (XIII)

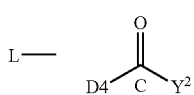  (XIII)

in which $Y^2$ is OH, $OC_1$-$C_4$-alkyl, Cl or together with CO is an activated ester group, and in which D4 is $C_0$-$C_9$-alkylene which can contain a group Z, with a compound of the formula (XIV)

Z²-D-E  (XIV)

in which $Z^2$ is OH or $NR^7$.

The compounds of the formula III are starting compounds for the preparation of compounds of the formulae V, VII, VIII. Compounds of the formula IIIa H—B-G  (IIIa)

are prepared by standard methods, as described, for example, in J. A. Kiristy et al., *J. Med. Chem.* 1978, 21, 1303 or C. B. Pollard, J. *Am. Chem. Soc.* 1934, 56, 2199, or by a) reacting a compound of the general formula (XV)

HB3  (XV)

in which B3 is

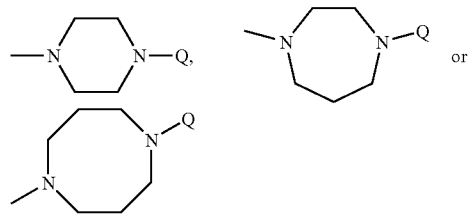

and Q is H or a customary amino protective group, e.g. butyloxycarbonyl, benzyl or methyl, with
a compound of the general formula (XVI)

Y⁴-G  (XVI)

in which $Y^4$ is $B(OH)_2$, —$SnBu_3$, trifluoromethanesulfonyloxy or has the meanings indicated for $Y^1$, in a known manner; or b) reacting a compound of the general formula (XVII)

Q-B4  (XVII)

in which B4 is

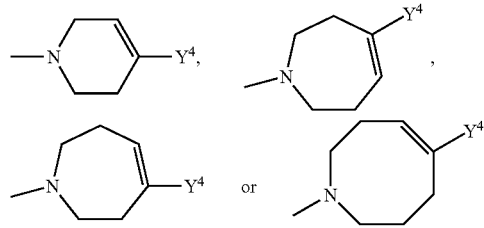

and $Y^4$ and Q have the meanings indicated above
with a compound of the general formula (XVIII)

Y⁵-G  (XVIII)

in which $Y^5$ is a boron derivative, such as, for example, $B(OH)_2$ or a metal-containing leaving group, e.g. $SnR_3$ (R=butyl or phenyl) or zinc halide, if $Y^4$ is halogen or trifluoromethylsulfonyloxy; or in which $Y^5$ is halogen or trifluoromethylsulfonyloxy if $Y^4$ is a boron derivative, such as, for example, $B(OH)_2$ or a metal-containing leaving group, e.g. $SnR^3$ (R=butyl or phenyl) or zinc halide, according to known processes, as described, for example, in S. Buchwald et al., *Angew. Chem.* 1995, 107, 1456 or J. F. Hartweg et al., *Tetrahedron Lett* 1995, 36, 3604 or J. K. Stille et al., *Angew. Chem.* 1986, 98, 504 or Pereyre M. et al., "Tin in Organic Synthesis", Butterworth 1987; or c) reacting a compound of the general formula (XIX)

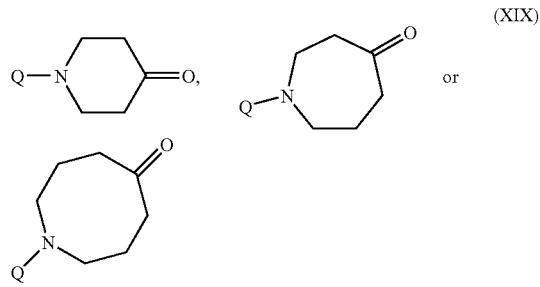  (XIX)

with a compound M-G,
in which M is a metal such as, for example, Li, $MgY^6$ and $Y^6$ is bromine, chlorine or iodine.

M-G can be obtained according to methods known from the literature.

Compounds of type B are either known or can be prepared analogously to known processes, such as, for example
1,4- and 1,5-diazacycloalkanes:
L. Börjeson et al. Acta Chem. Scand. 1991, 45, 621
Majahrzah et al Acta Pol. Pharm., 1975, 32, 145
1,4-diazacyclooct-6-enes:
W. Schroth et al. Z. Chem. 1969, 9, 143
1-azacyclooctanones:
N. J. Leonard et al. J. Org. Chem. 1964, 34, 1066
1-azacycloheptanones:
A. Yokoo et al. Bull Chem. Soc. Jpn. 1956, 29, 631
Compounds of type L and G are either known or can be prepared according to known processes, as described, for example, in A. R. Katritzky, C W. Rees (ed.) "Comprehensive Heterocyclic Chemistry", Pergamon Press, or "The Chemistry of Heterocyclic Compounds", J. Wiley & Sons Inc. NY and the references cited there or the patent literature cited above A process for the preparation of compounds of the general formula (Ib)

L1a-D-E2  (Ib)

consists in
a) reacting a compound of the general formula (XX)

L1a-D-C(O)-A  (XX)

with a compound of the formula E2
in which A is H or OH,
under reductive conditions analogously to methods known from the literature, as described, for example, in *J. Org. Chem.* 1986, 50, 1927; or WO 92/20655, or b) for the preparation of a compound of the formula (Ib1)

L1a-D-E2a  (Ib1)

reacting compounds of the general formula (XXII) or (XXIII),

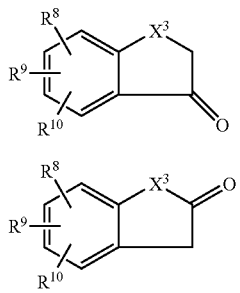

(XXII)

(XXIII)

with a compound of the general formula (XXIV)

L1a-D-Z$^4$H  (XXIV)

where Z$^4$ is NR$^{11}$ and R$^{11}$ has the meanings indicated above, under reductive conditions.

Compounds of type (XXIV) can be synthesized by reacting compounds of the formula (II) by means of Gabriel synthesis to give the corresponding amine (XXV)

L-D-NH$_2$  (XXV)

then first linking it with R$^{11}$ (using the corresponding aldehyde or by means of alkylation in the presence of a base) and subsequently with E2 in a reductive amination, as described, for example, in *J. Org. Chem.* 1986, 50, 1927).

Compounds of the general formula (XXV) can also be obtained by reaction of compounds of the formula (II) with azides, such as, for example, sodium azide, and subsequent reduction, as described, for example, in H. Staudinger, *Helv. Chim. Acta* 1985, 2, 635 or
R. Carrie, *Bull. Chem. Soc. Fr.* 1985, 815.

Compounds of the formula (XXII) and (XXIII) are either known from the literature or can be prepared by known methods, as described, for example, in A. van Vliet et al. *J. Med. Chem.* 1996, 39, 4233
M. Langlois *Bioorg. Med. Chem. Lett.* 1993, 3, 2035
U. Hacksell *J. Med. Chem.* 1993, 36, 4221
or in WO 93/08799 or WO 95/04713.

If E2 is a radical of the general formula (XXVI)

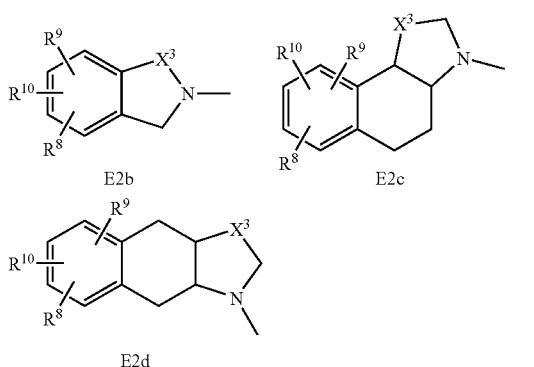

(XXVI)

in which R$^8$, R$^9$, R$^{10}$, X$^3$ have the meanings indicated above, the corresponding amines can be prepared as described, for example, in S. Smith et al., *Bioorg. Med. Chem. Lett.* 1998, 8, 2859;
WO 97/47602 or WO 920655 or
J. Med. Chem. 1987, 30, 2111 and 2208.

The compounds of the formula (IV) are either known or can be prepared according to known processes, such as described, for example, in A. R. Katrizky, C. W. Rees (ed.) "Comprehensive Heterocyclic Chemistry", Pergamon Press, or "The Chemistry of Heterocyclic Compounds" J. Wiley & Sons Inc. NY and the references cited there or in S. Kubota et al. *Chem. Pharm. Bull* 1975, 23, 955 or Vosilevskii et al. Izv. Akad. Nauk. SSSR Ser. Khim 1975, 23, 955.

The following examples serve to illustrate the invention without restricting it.

EXAMPLE 1

4'-Acetylbiphenyl-4-carboxylic acid N-(4-(4-(2-methoxyphenyl)piperazin-1-yl)but-1-yl)amide

EXAMPLE 2

Thienyl-2-carboxylic acid N-(4-(4-(2,3-dichlorophenyl)piperazin-1-yl)but-1-yl)amide

EXAMPLE 3

3-(4-(4-(2-t-Butyl-6-trifluoromethyl)pyrimidin-4-yl)piperazin-1-yl)but-2-ylmercapto)-4-methyl-5-methylamino-1,2,4-(4H)-triazole

EXAMPLE 4

3-(4-(4-(2-t-Butyl-6-trifluoromethyl)pyrimidin-4-yl)piperazin-1-yl)2-methyleneprop-1-yl-mercapto)5-methylamino-1,2,4-(4H)-triazole

EXAMPLE 5

5-Amino-3-(4-(4-(2-t-butyl-6-trifluoromethyl)pyrimidin-4-yl)homo-piperazin-1-yl)2-methyl-but-2-en-1-ylmercapto)-4-methyl-1,2,4-(4H)-triazole

EXAMPLE 6

3-(4-(4-(2-t-Butyl-6-trifluoromethyl)pyrimidin-4-yl)piperazin-1-yl)prop-1-ylmercapto)-4-methyl-5-methylamino-1,2,4-(4H)-triazole

EXAMPLE 7

5-Amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole

EXAMPLE 8

5-Amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole

EXAMPLE 9

5-Amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole

EXAMPLE 10

2-(3-(4-(2-t-Butyl-6-trifluoromethyl)pyrimidin-4-yl)piperazin-1-yl)propoxy-pyrimidin-4-ol

EXAMPLE 11

2-(3-(4-(2-t-Butyl-6-trifluoromethyl)pyrimidin-4-yl)piperazin-1-yl)propylmercaptopyrimidin-4-ol fumarate

EXAMPLE 12

2-Naphthoic acid N-(4-(4-(2-t-butyl-6-trifluoromethyl)pyrimidin-4-yl)homopiperazin-1-yl)but-1-ylamide

EXAMPLE 13

5-Amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole

EXAMPLE 14

3-(4-(4-(2-t-Butyl-6-trifluoromethyl)pyrimidin-4-yl)piperazin-1-yl)prop-1-ylmercapto-5-(2,5-dimethylfur-3-yl)4-methyl-1,2,4-(4H)-triazole

EXAMPLE 15

(4-(4-(2-t-Butyl-6-trifluoromethyl)pyrimidin-4-yl)homopiperazin-1-yl)prop-1-ylmercapto-4-methyl-5-(4-methylpyrazol-5-yl)1,2,4-(4H)-triazole

EXAMPLE 16

4-Methyl-5-phenyl-1,2,4-(4H)-triazole-3-carboxylic acid N-(4-(4-(2-t-butyl-6-trifluoromethyl)pyrimidin-4-yl)homo-piperazin-1-yl)but-1-yl-amide

EXAMPLE 17

5-Amino-2-(8-(4-(3-cyanophenyl)piperazin-1-yl)octyl-1-ylmercapto)1,3,4-thiadiazole

EXAMPLE 18

2-(3-(5-(3-(Trifluoromethylphenyl)-1,5-diazocin-1-yl)-propyl-mercapto)pyrimidin-4-ol

EXAMPLE 19

3-(4-(4-(2-t-Butyl-6-trifluoromethyl)pyrimidin-4-yl)piperazin-1-yl)but-1-ylpyrimidin-4-ol

EXAMPLE 20

4-Methoxybenzoic acid N-(4-(4-(2-t-butyl-6-trifluoromethyl)-pyrimidin-4-yl)homopiperazin-1-yl)but-1-ylamide

EXAMPLE 21

1-Benzothiophene-2-carboxylic acid N-(4-(4-(2-t-butyl-6-trifluoromethyl)pyrimidin-4-yl)piperazin-1-yl)but-1-ylamide

EXAMPLE 22

5-Methoxybenzofuran-2-carboxylic acid N-(4-(4-(2-t-butyl-6-trifluoromethyl)pyrimidin-4-yl)homopiperazin-1-yl)but-1-ylamide

EXAMPLE 23

(E)-N-({2-[(7-Cyano-3,4-dihydro-2(1H)-isoquinolinyl)methyl]-cyclopropyl}methyl)-3-(1H-indol-5-yl)-2-propenamide

EXAMPLE 24

2-(4-{[(E)-3-(1H-Indol-5-yl)-2-propenoyl]amino}butyl)-1,2,3,4-tetrahydro-7-isoquinolinyl trifluoromethanesulfonate Surprisingly, by the use of such dopamine $D_3$ receptor ligands for the production of drugs for controlling kidney function disorders a specific improvement in pathophysiological disorders of filtration can be achieved.

The action of the dopamine $D_3$ antagonists was investigated in an animal experimental model of diabetic nephropathy. Rats in which diabetes mellitus had been induced by administration of streptozotocin developed marked glomerular hyperfiltration within 14 days. If rats in which diabetes mellitus had been induced in this manner were treated subchronically with a dopamine $D_3$ receptor antagonist, the diabetic hyperfiltration did not occur.

The $D_3$ receptor ligands can also be employed in combination with other active compounds for the production of drugs for treating the syndromes mentioned. ACE inhibitors such as, for example, trandolapril and $AT_1$ antagonists such as, for example, losartan are particularly suitable for such a combination. Furthermore, a combination with calcium antagonists or with β-blockers can also be carried out.

Methods 60 mg/kg of streptozotocin, dissolved in citrate buffer (21 mg of citric acid per 1 ml of double-distilled water), were injected intraperitoneally into male Sprague-Dawley rats having a body weight of 180 to 200 g. Diabetes mellitus was regarded as being induced successfully when an evening glucose concentration of at least 180 mg/dl was found in the venous blood after 24 hours. The blood glucose values of the diabetic animals were between 350 and 450 mg/dl. Insulin substitution was thus not necessary. The body weight of the experimental animals increased about 5 g per day. The same volume of citrate buffer was injected intraperitoneally into nondiabetic time control animals (CON). They had blood glucose values of between 90 and 1120 mg/dl.

Immediately after successful determination of diabetes mellitus, the animals were accommodated in normal cages with standard feed (Altromin 1320) and mains water ad libitum. By means of different medicinal treatment (administration of the substances via the drinking water), the following four experimental groups were formed:
  CON (1) nondiabetic animals without additional treatment (time control)
  DM-VHC (2) diabetic animals without additional treatment (diabetic control)
  DM-SUL (3) diabetic animals with S-sulpiride treatment (25 mg/kg/d)
  DM-D3 (4) diabetic animals with $D_3$-A treatment ($D_3$-A1: $D_3$ receptor antagonist according to Example (7) (5 mg/kg/d); $D_3$-A2: $D_3$ receptor antagonist according to Example (11))

The volume of liquid absorbed was recorded daily. Every third day, the body weight and the blood glucose level of the animals were determined. After 12 days, the experimental animals were kept in metabolic cages for 24 hours for urine collection. The protein concentration in the urine was determined according to the standard method described by Lowry. For this, after incubation of the samples with 1 M NaOH a color reaction was induced with Folin reagent (phenol-Ciocalteu's), whose intensity was quantified photometrically. The albumin concentration in the urine was determined by a radioimmunoassay (RIA) specific for albumin. A kit from Biermann (KHAD 2: albumin RIA), was employed which used a polyclonal antibody against human serum albumin (goat) and $^{125}$I-labeled human serum albumin as a tracer. After 14 to 16 days, the animals were anesthetized with thiopental (80 mg/kg) and polyethylene catheters were placed in the jugular vein and the carotid artery and also in the urinary bladder. The glomerular filtration rate (GFR) was determined by means of the renal $^3$H-inulin clearance. The mean arterial blood pressure (MAP) and the heart rate (HR) were furthermore recorded during the experiment. At the end of the clearance experiments, the kidneys were removed and subjected to a histopathological examination.

Results

In the 24-hour urine collection of conscious animals, a marked proteinuria (133 vs. 46 mg/d) and an even more marked albuminuria (118 vs. 23 µg/d) was seen as an expression of the damage to the glomerular filtration barrier in the untreated diabetic animals compared with the time controls. In the diabetic animals treated with sulpiride, this pathological albuminuria was only slightly reduced (101 µg/d) and the proteinuria was even further increased (178 mg/d). In contrast to this, in the animals treated with $D_3$-A according to Example 7 the proteinuria was decreased (113 mg/d) and the albuminuria was completely suppressed with only 18 µg/d.

The selectivity for sulpiride and $D_3$-A1 is as described for Example 42 in WO 96/02520.

In the clearance investigation, the anesthetized untreated diabetic animals (2) showed a markedly increased glomerular filtration rate (1.10 vs. 0.83 ml/min) compared with the time controls as a sign of the diabetic glomerular hyperfiltration. Both in sulpiride- and in $D_3$-A-treated diabetic animals ((3) and (4)), this diabetic hyperfiltration was suppressed and the animals showed an almost normal GFR (0.71 and 0.83 ml/min, respectively).

In the untreated diabetic animals (2) in comparison with healthy time controls (1), in addition to on the whole hypertrophically enlarged kidneys, the histopathological investigation showed a significant enlargement of the glomeruli (expressed by the mean value of 20 microscopically measured areas each). This glomerular hypertrophy was likewise to be observed in the diabetic animals with sulpiride treatment (3), but not in the diabetic animals which had been treated with $D_3$-A1 (4).

The normal wet weight of the kidneys of nondiabetic adult rats was 0.9±0.1 g per 100 g body weight. In diabetic rats (DM-VHC) the kidney wet weight was 1.1+0.04 g per 100 g body weight, which indicates incipient hypertrophy. Treatment with $D_3$-A2 normalized the kidney wet weight to 0.96+ 0.03 g per 100 g body weight.

In summary, these data ascertained on an in-vivo model of diabetes mellitus show that the subchronic treatment with pharmacological inhibitors of dopamine $D_2$ receptors (sulpiride) and of dopamine $D_3$ receptors ($D_3$-A) leads to a significant decrease in the renal hemodynamic changes in the course of diabetic nephropathy.

Subchronic treatment with $D_3$-A2 (30 mg/kg body weight per day) distinctly reduced the glomerular hyperfiltration and the diabetes-induced renal hyperperfusion. There was likewise a distinct reduction in the incipient renal hypertrophy.

The comparison of the treatment groups moreover showed that the structural eliminated intrarenal changes occurring in diabetic nephropathy were abolished by the dopamine $D_3$ receptor antagonists $D_3$-A1 and $D_3$-A2, but not by the dopamine $D_2$ receptor antagonist sulpiride. Functionally, this difference was also manifested in the markedly reduced pathological protein and albumin excretion, which is regarded as an important marker of the increasing functional impairment of the kidneys, by the dopamine $D_3$ receptor antagonist $D_3$-A, but not by the dopamine $D_2$ antagonist sulpiride. Altogether, the results of this investigation give a clear indication that the administration of dopamine $D_3$ receptor antagonists such as, for example, $D_3$-A can favorably influence the course of diabetic nephropathy.

We claim:

1. A method for the treatment of a renal function disorder comprising administering an effective amount of dopamine $D_3$ receptor antagonists to a patient in need thereof, wherein the renal function disorder is selected from the group consisting of renal function disorders with glomerular hyperfiltration,
renal function disorders caused by diabetes mellitus,
renal function disorders caused by nonrenal hypertension,
renal function disorders caused by glomerulonephritis,
renal function disorders caused by ascending urinary tract infections,
renal function disorders caused by sickle cell anemia,
renal function disorders caused by compensatory hypertrophy after unilateral nephrectomy, and
renal function disorders caused by mesangial dysfunction.

2. The method as claimed in claim 1, wherein the receptor antagonist is 5-amino-3-(4-(4-(2-t-butyl-6-trifluoromethyl)pyrimidin-4-yl)-piperazin-1-yl)-2-methylbut-2-eny-1-ylmercapto)-4-methyl-1,2,4-(4H)-triazole or 2-(3-(4-(2-t-butyl-6-trifluoromethyl)pyrimidin-4-yl)piperazin-1-yl)propylmercaptopyrimidin-4-ol fumarate.

3. The method of claim 1, wherein the dopamine $D_3$ receptor antagonist is selected from the group consisting of 4'-acetylbiphenyl-4-carboxylic acid N-(4-(4-(2-methoxyphenyl)piperazin-1-yl)but-1-yl)amide,
thienyl-2-carboxylic acid N-(4-(4-(2,3-dichlorophenyl)piperazin-1-yl)but-1-yl)amide,
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole,
5-amino-3-(4-(4-(2-t-butyl-6-trifluoromethyl)pyrimidin-4-yl)homo-piperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole,
5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole,
5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole,
5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol,
2-(3-(4-(2-t-butyl-6-trifluoromethyl)pyrimidin-4-yl)piperazin-1-yl)propylmercaptopyrimidin-4-ol fumarate,
2-naphthoic acid N-(4-(4-(2-t-butyl-6-trifluoromethyl)pyrimidin-4-yl)homopiperazin-1-yl)but-1-ylamide,
5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole,
(4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole,
4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide,
5-amino-2-(8-(4-(3-cyanophenyl) piperazin-1-yl) octyl-1-yl-mercapto) 1,3,4-thiadiazole,
2-(3-(5-(3-(trifluoromethylphenyl)-1,5-diazocin-1-yl)-propyl-mercapto)pyrimidin-4-ol,
3-(4-(4-(2-t-butyl-6-trifluoromethyl)pyrimidin-4-yl)piperazin-1-yl)but-1-ylpyrimidin-4-ol,
4-methoxybenzoic acid N-(4-(4-(2-t-butyl-6-trifluoromethyl)pyrimidin-4-yl)homopiperazin-1-yl)but-1-ylamide,
1-benzothiophene-2-carboxylic acid N-(4-(4-(2-t-butyl-6-trifluoromethyl)pyrimidin-4-yl) piperazin-1-yl)but-1-ylamide,
5-methoxybenzofuran-2-carboxylic acid N-(4-(4-(2-t-butyl-6-trifluoromethyl)pyrimidin-4-yl) homopiperazin-1-yl)but-1-ylamide,
(E)-N-({2-[(7-cyano-3,4-dihydro-2(1H)-isoquinolinyl]methyl]cyclopropyl}methyl)-3-(1H-indol-5-yl)-2-propenamide and
2-(4-{[(E)-3-(1H-indol-5-yl)-2-propenoyl]amino}butyl)-1,2,3,4-tetrahydro-7-isoquinolinyl trifluoromethanesulfonate.

4. The method of claim 1, wherein the dopamine $D_3$ receptor antagonist is selected from the group consisting of
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole,
5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole,
5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole,
5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole,
5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole,
2-(3-(4-(2-t-butyl-6-trifluoromethyl)pyrimidin-4-yl)piperazin-1-yl)propoxy-pyrimidin-4-ol,
2-(3-(4-(2-t-butyl-6-trifluoromethyl)pyrimidin-4-yl)piperazin-1-yl)propylmercaptopyrimidin-4-ol fumarate,
5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole,
(4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole,
4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide,
3-(4-(4-(2-t-butyl-6-trifluoromethyl)pyrimidin-4-yl)piperazin-1-yl)but-1-ylpyrimidin-4-ol and 4-methoxyben-

5. The method of claim 1, wherein the dopamine $D_3$ receptor antagonist is selected from the group consisting of
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole,
5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole,
5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole,
5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole,
5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole,
2-(3-(4-(2-t-butyl-6-trifluoromethyl)pyrimidin-4-yl)piperazin-1-yl)propoxy-pyrimidin-4-ol,
2-(3-(4-(2-t-butyl-6-trifluoromethyl)pyrimidin-4-yl)piperazin-1-yl)propylmercaptopyrimidin-4-ol fumarate,
5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole,
(4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole,
4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide,
3-(4-(4-(2-t-butyl-6-trifluoromethyl)pyrimidin-4-yl)piperazin-1-yl)but-1-ylpyrimidin-4-ol and 4-methoxybenzoic acid N-(4-(4-(2-t-butyl-6-trifluoromethyl)pyrimidin-4-yl)homopiperazin-1-yl)but-1-ylamide.

6. A method for the treatment of a renal function disorder associated with glomerular hyperfiltration in a patient which comprises administering to said patient an effective amount of a dopamine D₃ receptor antagonist.

7. The method of claim 6, wherein the dopamine D₃ receptor antagonist is selected from the group consisting of 4'-acetylbiphenyl-4-carboxylic acid N-(4-(4-(2-methoxyphenyl)-piperazin-1-yl)but-1-yl)amide, thienyl-2-carboxylic acid N-(4-(4-(2,3-dichlorophenyl)piperazin-1-yl)but-1-yl)amide, 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 2-naphthoic acid N-(4-(4-(2-t-butyl-6-trifluoromethyl)pyrimidin-4-yl)homopiperazin-1-yl)but-1-ylamide, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylicacid N-(4-(4-(2-t-butyl-6-trifluoromethyl)pyrimidin-4-yl)homopiperazin-1-yl)-but-1-yl-amide, 5-amino-2-(8-(4-(3-cyanophenyl)piperazin-1-yl)octyl-1-yl-mercapto)1,3,4-thiadiazole, 2-(3-(5-(3-(trifluoromethylphenyl)-1,5-diazocin-1-yl)-propylmercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide, 5-methoxybenzofuran-2-carboxylic acid N-(4-(4-(2-t-butyl-6-trifluoromethyl)pyrimidin-4-yl)homopiperazin-1-yl)but-1-ylamide, (E)-N-({2-[(7-cyano-3,4-dihydro-2(1H)-isoquinolinyl)methyl]cyclopropyl}methyl)-3-(1H-indol-5-yl)-2-propenamide and 2-(4-{[(E)-3-(1H-indol-5-yl)-2-propenoyl]amino}butyl)-1,2,3,4-tetrahydro-7-isoquinolinyl trifluoromethanesulfonate.

8. The method of claim 6, wherein the dopamine D₃ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 2-(3-(5-(3-(trifluoromethylphenyl)-1,5-diazocin-1-yl)-propyl-mercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide and 5-methoxybenzofuran-2-carboxylic acid N-(4-(4-(2-t-butyl-6-trifluoromethyl)pyrimidin-4-yl)homopiperazin-1-yl)but-1-ylamide.

9. The method of claim 6, wherein the dopamine D₃ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)-2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 3-(4-(4-(2-t-butyl-6-trifluoromethyl)pyrimidin-4-yl)piperazin-1-yl)but-1-ylpyrimidin-4-ol and 4-methoxybenzoic acid N-(4-(4-(2-t-butyl-6-trifluoromethyl)pyrimidin-4-yl)homopiperazin-1-yl)but-1-ylamide.

10. The method as claimed in claim 6, wherein the receptor antagonist is 5-amino-3-(4-(4-(2-t-butyl-6-trifluoromethyl)pyrimidin-4-yl)-piperazin-1-yl)-2-methylbut-2-eny-1-ylmercapto)-4-methyl-1,2,4-(4H)-triazole or 2-(3-(4-(2-t-butyl-6-trifluoromethyl)pyrimidin-4-yl)piperazin-1-yl)propylmercaptopyrimidin-4-ol fumarate.

11. A method for the treatment of a renal function disorder associated with albuminurea in a patient which comprises administering to said patient an effective amount of a dopamine $D_3$ receptor antagonist.

12. The method of claim 11, wherein the dopamine $D_3$ receptor antagonist is selected from the group consisting of 4'-acetylbiphenyl-4-carboxylic acid N-(4-(4-(2-methoxyphenyl)piperazin-1-yl)but-1-yl)amide, thienyl-2-carboxylic acid N-(4-(4-(2,3-dichlorophenyl)piperazin-1-yl)but-1-yl)amide, 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homo-piperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 2-naphthoic acid N-(4-(4-(2-t-butyl-6-trifluoromethyl)pyrimidin-4-yl)homopiperazin-1-yl)but-1-ylamide, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 5-amino-2-(8-(4-(3-cyanophenyl)piperazin-1-yl)octyl-1-yl-mercapto)1,3,4-thiadiazole, 2-(3-(5-(3-(trifluoromethylphenyl)-1,5-diazocin-1-yl)-propyl-mercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide, 5-methoxybenzofuran-2-carboxylic acid N-(4-(4-(2-t-butyl-6-trifluoromethyl)pyrimidin-4-yl)homopiperazin-1-yl)but-1-ylamide, (E)-N-({2-[(7-cyano-3,4-dihydro-2(1H)-isoquinolinyl)methyl]cyclopropyl}methyl)-3-(1H-indol-5-yl)-2-propenamide and 2-(4-{[(E)-3-(1H-indol-5-yl)-2-propenoyl]amino}butyl)-1,2,3,4-tetrahydro-7-isoquinolinyl trifluoromethanesulfonate.

13. The method of claim 11, wherein the dopamine $D_3$ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)but-1-yl-amide, 2-(3-(5-(3-(trifluoromethylphenyl)-1,5-diazocin-1-yl)propylmercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide and 5-methoxybenzofuran-2-carboxylic acid N-(4-(4-(2-t-butyl-6-trifluoromethyl)pyrimidin-4-yl)homopiperazin-1-yl)but-1-ylamide.

14. The method of claim 11, wherein the dopamine $D_3$ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-2-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 3-(4-(4-(2-t-butyl-6-trifluoromethyl)pyrimidin-4-yl)piperazin-1-yl)but-1-ylpyrimidin-4-ol and 4-methoxybenzoic acid N-(4-(4-(2-t-butyl-6-trifluoromethyl)pyrimidin-4-yl)homopiperazin-1-yl)but-1-ylamide.

15. The method as claimed in claim 11, wherein the receptor antagonist is 5-amino-3-(4-(4-(2-t-butyl-6-trifluoromethyl)pyrimidin-4-yl)-piperazin-1-yl)-2-methylbut-2-eny-1-ylmercapto)-4-methyl-1,2,4-(4H)-triazole or 2-(3-(4-(2-t-butyl-6-trifluoromethyl)pyrimidin-4-yl)piperazin-1-yl)propylmercaptopyrimidin-4-ol fumarate.

16. A method for the treatment of a renal function disorder associated with glomerular hypertrophy in a patient which comprises administering to said patient an effective amount of a dopamine $D_3$ receptor antagonist.

17. The method of claim 16, wherein the dopamine $D_3$ receptor antagonist is selected from the group consisting of 4'-acetylbiphenyl-4-carboxylic acid N-(4-(4-(2-methoxyphenyl)piperazin-1-yl)but-1-yl)amide, thienyl-2-carboxylic acid N-(4-(4-(2,3-dichlorophenyl)piperazin-1-yl)but-1-yl)amide, 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole, 5-amino-3-(4-(4-(2-t-butyl-6-trifluoromethyl)pyrimidin-4-yl)homo-piperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 2-naphthoic acid N-(4-(4-(2-t-butyl-6-trifluoromethyl)pyrimidin-4-yl)homopiperazin-1-yl)but-1-ylamide, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 5-amino-2-(8-(4-(3-cyanophenyl)piperazin-1-yl)octyl-1-yl-mercapto)1,3,4-thiadiazole, 2-(3-(5-(3-(trifluoromethylphenyl)-1,5-diazocin-1-yl)-propyl-mercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide, 5-methoxybenzofuran-2-carboxylic acid N-(4-(4-(2-t-butyl-6-trifluoromethyl)pyrimidin-4-yl)homopiperazin-1-yl)but-1-ylamide, (E)-N-({2-[(7-cyano-3,4-dihydro-2(1H)-isoquinolinyl)methyl]cyclopropyl}methyl)-3-(1H-indol-5-yl)-2-propenamide and 2-(4-{[(E)-3-(1H-indol-5-yl)-2-propenoyl]amino}butyl)-1,2,3,4-tetrahydro-7-isoquinolinyl trifluoromethanesulfonate.

18. The method of claim 16, wherein the dopamine $D_3$ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 2-(3-(5-(3-(trifluoromethylphenyl)-1,5-diazocin-1-yl)propylmercapto)pyrimidin-4-ol, 3-(4-(4-(2-t-butyl-6-trifluoromethyl)pyrimidin-4-yl)piperazin-1-yl)but-1-ylpyrimidin-4-ol, 4-methoxybenzoic acid N-(4-(4-(2-t-butyl-6-trifluoromethyl)pyrimidin-4-yl)homopiperazin-1-yl)but-1-ylamide, 1-benzothiophene-2-carboxylic acid N-(4-(4-(2-t-butyl-6-trifluoromethyl)pyrimidin-4-yl)piperazin-1-yl)but-1-ylamide and 5-methoxybenzofuran-2-carboxylic acid N-(4-(4-(2-t-butyl-6-trifluoromethyl)pyrimidin-4-yl)homopiperazin-1-yl)but-1-ylamide.

19. The method of claim 16, wherein the dopamine $D_3$ receptor antagonist is selected from the group consisting of 3-(4-(4-(2-t-butyl-6-trifluoromethyl)pyrimidin-4-yl)piperazin-1-yl)but-2-ylmercapto)-4-methyl-5-methylamino-1,2,4-(4H)-triazole, 3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole, 5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)-piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 3-(4-(4-(2-t-butyl-6-trifluoromethyl)pyrimidin-4-yl)piperazin-1-yl)but-1-ylpyrimidin-4-ol and 4-methoxybenzoic acid N-(4-(4-(2-t-butyl-6-trifluoromethyl)pyrimidin-4-yl)homopiperazin-1-yl)but-1-ylamide.

20. The method as claimed in claim 16, wherein the receptor antagonist is 5-amino-3-(4-(4-(2-t-butyl-6-trifluoromethyl)pyrimidin-4-yl)-piperazin-1-yl)-2-methylbut-2-eny-1-ylmercapto)-4-methyl-1,2,4-(4H)-triazole or 2-(3-(4-(2-t-butyl-6-trifluoromethyl)pyrimidin-4-yl)piperazin-1-yl)propylmercaptopyrimidin-4-ol fumarate.

21. A method for the treatment of diabetic nephropathy comprising administering an effective amount of dopamine $D_3$ receptor antagonists to a patient in need thereof.

22. The method as claimed in claim 21, wherein the receptor antagonist is 5-amino-3-(4-(4-(2-t-butyl-6-trifluoromethyl)pyrimidin-4-yl)-piperazin-1-yl)-2-methylbut-2-eny-1-ylmercapto)-4-methyl-1,2,4-(4H)-triazole or 2-(3-(4-(2-t-butyl-6-trifluoromethyl)pyrimidin-4-yl)piperazin-1-yl)propylmercaptopyrimidin-4-ol fumarate.

23. The method of claim 21, wherein the dopamine D₃ receptor antagonist is selected from the group consisting of
4'-acetylbiphenyl-4-carboxylic acid N-(4-(4-(2-methoxyphenyl)piperazin-1-yl)but-1-yl)amide,
thienyl-2-carboxylic acid N-(4-(4-(2,3-dichlorophenyl) piperazin-1-yl)but-1-yl)amide,
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole,
5-amino-3-(4-(4-(2-t-butyl-6-trifluoromethyl)pyrimidin-4-yl)homo-piperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole,
5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole,
5-amino-3-(4-(4-(2-t-butyl-6-n-propyl)pyrimidin-4-yl) piperazin-1-yl)2-methyl-prop-1-en-1-ylmercapto)-4-methyl-1,2,4-(4H)-triazole,
5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole,
2-(3-(4-(2-t-butyl-6-trifluoromethyl)pyrimidin-4-yl)piperazin-1-yl)propoxy-pyrimidin-4-ol,
2-(3-(4-(2-t-butyl-6-trifluoromethyl)pyrimidin-4-yl)piperazin-1-yl)propylmercaptopyrimidin-4-ol fumarate,
2-naphthoic acid N-(4-(4-(2-t-butyl-6-trifluoromethyl)pyrimidin-4-yl)homopiperazin-1-yl)but-1-ylamide,
5-amino-3-(4-(4-(2-t-butyl-6-n-propyl)pyrimidin-4-yl) piperazin-1-yl)-2-methylen-prop-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole,
(4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole,
4-methyl-5-phenyl-1,2,4-(4H)-triazole-3-carboxylicacid N-(4-(4-(2-t-butyl-6-trifluoromethyl)pyrimidin-4-yl) homopiperazin-1-yl)-but-1-yl-amide,
5-amino-2-(8-(4-(3-cyanophenyl)piperazin-1-yl)octyl-1-yl-mercapto)1,3,4-thiadiazole,
2-(3-(5-(3-(trifluoromethylphenyl)-1,5-diazocin-1-yl)-propyl-mercapto)pyrimidin-4-ol,
3-(4-(4-(2-t-butyl-6-trifluoromethyl)pyrimidin-4-yl)piperazin-1-yl)but-1-ylpyrimidin-4-ol,
4-methoxybenzoic acid N-(4-(4-(2-t-butyl-6-trifluoromethyl)pyrimidin-4-yl)homopiperazin-1-yl)but-1-ylamide,
1-benzothiophene-2-carboxylic acid N-(4-(4-(2-t-butyl-6-trifluoromethyl)pyrimidin-4-yl)piperazin-1-yl)but-1-ylamide,
5-methoxybenzofuran-2-carboxylic acid N-(4-(4-(2-t-butyl-6-trifluoromethyl)pyrimidin-4-yl)homopiperazin-1-yl)but-1-ylamide,
(E)-N-({2-[(7-cyano-3,4-dihydro-2(1H)-isoquinolinyl) methyl]cyclopropyl}methyl)-3-(1H-indol-5-yl)-2-propenamide and
2-(4-{[(E)-3-(1H-indol-5-yl)-2-propenoyl]amino}butyl)-1,2,3,4-tetrahydro-7-isoquinolinyl trifluoromethanesulfonate.

24. The method of claim 21, wherein the dopamine D₃ receptor antagonist is selected from the group consisting of
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)5-methylamino-1,2,4-(4H)-triazole,
5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole,
5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole,
5-amino-3-(4-(4-(2-t-butyl-6-n-propyl)pyrimidin-4-yl) piperazin-1-yl)2-methyl-prop-1-en-1-ylmercapto)-4-methyl-1,2,4-(4H)-triazole,
5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole,
2-(3-(4-(2-t-butyl-6-trifluoromethyl)pyrimidin-4-yl)piperazin-1-yl)propoxy-pyrimidin-4-ol,
2-(3-(4-(2-t-butyl-6-trifluoromethyl)pyrimidin-4-yl)piperazin-1-yl)propylmercaptopyrimidin-4-ol fumarate,
5-amino-3-(4-(4-(2-t-butyl-6-n-propyl)pyrimidin-4-yl) piperazin-1-yl)-2-methylen-prop-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole,
(4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole,
4-methyl-5-phenyl-1,2,4-(4H)-triazole-3-carboxylicacid N-(4-(4-(2-t-butyl-6-trifluoromethyl)pyrimidin-4-yl) homopiperazin-1-yl)-but-1-yl-amide,
2-(3-(5-(3-(trifluoromethylphenyl)-1,5-diazocin-1-yl)-propylmercapto)pyrimidin-4-ol,
3-(4-(4-(2-t-butyl-6-trifluoromethyl)pyrimidin-4-yl)piperazin-1-yl)but-1-ylpyrimidin-4-ol,
4-methoxybenzoic acid N-(4-(4-(2-t-butyl-6-trifluoromethyl)pyrimidin-4-yl)homopiperazin-1-yl)but-1-ylamide,
1-benzothiophene-2-carboxylic acid N-(4-(4-(2-t-butyl-6-trifluoromethyl)pyrimidin-4-yl)piperazin-1-yl)but-1-ylamide and
5-methoxybenzofuran-2-carboxylic acid N-(4-(4-(2-t-butyl-6-trifluoromethyl)pyrimidin-4-yl)homopiperazin-1-yl)but-1-ylamide.

25. The method of claim 21, wherein the dopamine D₃ receptor antagonist is selected from the group consisting of
3-(4-(4-(2-t-butyl-6-trifluoromethyl)pyrimidin-4-yl)piperazin-1-yl)but-2-ylmercapto)-4-methyl-5-methylamino-1,2,4-(4H)-triazole,
3-(4-(4-(2-t-butyl-6-trifluoromethyl)pyrimidin-4-yl)piperazin-1-yl)2-methyleneprop-1-yl-mercapto)-5-methylamino-1,2,4-(4H)-triazole,
5-amino-3-(4-(4-(2-t-butyl-6-trifluoromethyl)pyrimidin-4-yl)homopiperazin-1-yl)2-methyl-but-2-en-1-ylmercapto)-4-methyl-1,2,4-(4H)-triazole,
3-(4-(4-(2-t-butyl-6-trifluoromethyl)pyrimidin-4-yl)piperazin-1-yl)prop-1-ylmercapto)-4-methyl-5-methylamino-1,2,4-(4H)-triazole, 5-amino-3-(4-(4-(2-t-butyl-6-trifluoromethyl)pyrimidin-4-yl)-piperazin-1-yl)2-methyl-but-2-en-1-ylmercapto)-4-methyl-1,2,4-(4H)-triazole, 5-amino-3-(4-(4-(2-t-butyl-6-n-propyl)pyrimidin-4-yl)piperazin-1-yl)2-methyl-prop-1-en-1-ylmercapto)-4-methyl-1,2,4-(4H)-triazole, 5-amino-3-(4-(4-(2-t-butyl-6-trifluoromethyl)pyrimidin-4-yl)-piperazin-1-yl)2-methyl-but-2-ylmercapto)-4-methyl-1,2,4-(4H)-triazole, 2-(3-(4-(2-t-butyl-6-trifluoromethyl)pyrimidin-4-yl)piperazin-1-yl)propoxy-pyrimidin-4-ol, 2-(3-(4-(2-t-butyl-6-trifluoromethyl)pyrimidin-4-yl)piperazin-1-yl)propylmercaptopyrimidin-4-ol fumarate, 5-amino-3-(4-(4-(2-t-butyl-6-n-propyl)pyrimidin-4-yl)piperazin-1-yl)-2-methylen-prop-1-ylmercapto)-4-methyl-1,2,4-(4H)-triazole, 3-(4-(4-(2-t-butyl-6-trifluoromethyl)pyrimidin-4-yl)piperazin-1-yl)prop-1-ylmercapto-5-(2,5-dimethylfur-3-yl)4-methyl-1,2,4-(4H)-triazole, (4-(4-(2-t-butyl-6-trifluoromethyl)pyrimidin-4-yl)homopiperazin-1-yl)prop-1-ylmercapto-4-methyl-5-(4-methylpyrazol-5-yl)1,2,4-(4H)-triazole, 4-methyl-5-phenyl-1,2,4-(4H)-triazole-3-carboxylic acid N-(4-(4-(2-t-butyl-6-trifluoromethyl)pyrimidin-4-yl)homopiperazin-1-yl)-but-1-yl-amide, 3-(4-(4-(2-t-butyl-6-trifluoromethyl)pyrimidin-4-yl)piperazin-1-yl)but-1-ylpyrimidin-4-ol and 4-methoxybenzoic acid N-(4-(4-(2-t-butyl-6-trifluoromethyl)pyrimidin-4-yl)homopiperazin-1-yl)but-1-ylamide.

\* \* \* \* \*